United States Patent
Rauch et al.

(10) Patent No.: US 9,757,705 B2
(45) Date of Patent: Sep. 12, 2017

(54) METHOD FOR PRODUCTION OF CONCENTRATES OF PREFERABLY WATER-SOLUBLE ACTIVE AGENTS

(71) Applicant: KWIZDA AGRO GMBH, Vienna (AT)

(72) Inventors: Andreas Rauch, Vienna (AT); Andreas Mühlanger, Reinprechtspölla (AT)

(73) Assignee: KWIZDA AGRO GMBH, Vienna (AT)

( * ) Notice: Subject to any disclaimer, the term of this patent is extended or adjusted under 35 U.S.C. 154(b) by 0 days.

(21) Appl. No.: 14/912,878

(22) PCT Filed: Aug. 21, 2014

(86) PCT No.: PCT/EP2014/067836
§ 371 (c)(1),
(2) Date: Feb. 18, 2016

(87) PCT Pub. No.: WO2015/025001
PCT Pub. Date: Feb. 26, 2015

(65) Prior Publication Data
US 2016/0198715 A1    Jul. 14, 2016

(30) Foreign Application Priority Data
Aug. 21, 2013 (EP) .................. 13181187

(51) Int. Cl.
*A01N 47/40*   (2006.01)
*A01N 25/28*   (2006.01)
*A61K 8/92*    (2006.01)
*B01J 13/14*   (2006.01)
*A61K 9/50*    (2006.01)

(52) U.S. Cl.
CPC .......... *B01J 13/14* (2013.01); *A01N 25/28* (2013.01); *A61K 9/5026* (2013.01); *A61K 9/5015* (2013.01); *A61K 9/5031* (2013.01)

(58) Field of Classification Search
CPC ...... B01J 13/14; A61K 9/5015; A61K 9/5026; A61K 9/5031; A01N 25/28
See application file for complete search history.

(56) References Cited

U.S. PATENT DOCUMENTS

| 5,597,780 A | 1/1997 | Lee et al. |
| 5,911,923 A | 6/1999 | Work et al. |
| 6,020,066 A * | 2/2000 | Weisser .................. B01J 13/16 264/4.1 |
| 2010/0112318 A1 * | 5/2010 | McIntyre ................. B01J 13/14 428/206 |
| 2011/0021398 A1 * | 1/2011 | Allef ........................ A61K 8/25 510/138 |

FOREIGN PATENT DOCUMENTS

| CN | 101781851 | * 7/2010 |
| DE | 102004059977 | 7/2005 |
| DE | 102010028826 | 11/2011 |
| EP | 0841088 | 5/1998 |
| WO | WO 96/14743 | 5/1996 |
| WO | WO 2005/056700 | 6/2005 |
| WO | WO 2005/061087 | 7/2005 |
| WO | WO 2006/064193 | 6/2006 |
| WO | WO 2008/107658 | 9/2008 |
| WO | WO2011/017480 | 2/2011 |
| WO | WO 2011/141745 | 11/2011 |
| WO | WO 2012/069805 | 5/2012 |

* cited by examiner

*Primary Examiner* — Mina Haghighatian
(74) *Attorney, Agent, or Firm* — Norton Rose Fulbright US LLP

(57) ABSTRACT

The invention relates to a method for production of concentrates of water-soluble active agents, wherein, in a waterless method using solid active agents as starting materials, the crystals of an active agent are uniformly distributed in a first organic solvent to which a dispersing agent is added, the viscosity of the solution thus obtained is adjusted as applicable by a suitable auxiliary agent, a polymer creator is added to the solution thus obtained, in a second organic solvent as applicable, wherein the viscosity of either the solution to be added or the solution to be obtained is adjusted by the addition of a suitable auxiliary agent, and a cross-linking agent having at least two functional groups in a third organic solvent is given to the obtained solution, wherein the viscosity of either the added or obtained solution is in turn adjusted by the addition of a suitable auxiliary agent and the polymer creator is selected from the group comprising low-viscosity polymethylene-polyphenylisocyanate, preferably having an average NCO content of 25-35, particularly preferably 30-32%, and mixtures thereof.

15 Claims, No Drawings

METHOD FOR PRODUCTION OF CONCENTRATES OF PREFERABLY WATER-SOLUBLE ACTIVE AGENTS

CROSS-REFERENCE TO RELATED APPLICATIONS

This application is a national phase application under 35 U.S.C. §371 of International Application No. PCT/EP2014/067836 filed 21 Aug. 2014, which claims priority to European Patent Application No. 13181187.9 filed 21 Aug. 2013. The entire contents of each of the above-referenced disclosures is specifically incorporated by reference herein without disclaimer.

The present invention relates to a method for encapsulating a solid, water-soluble active agent or mixture of active agents by providing a coating, wherein by the coating the water-solubility of the coated particles is at least reduced in a defined manner, but is especially delayed for such a period of time until the desired effect of the active agent or mixture of active agents is obtained.

Numerous active ingredients exist in crystalline form with a water solubility in the range of a few grams per liter, typically from 0.1 to 50 g/l. This characteristic impedes or prevents both the formulation in the form of stable suspensions due to recrystallization during temperature changes, as well as an application under humid conditions, because after application rainfall, soil moisture, cleaning procedures, etc. will cause a washout (so-called "leaching") of the active agents. This leads to a reduced effect and unwanted entry of active agents for example into waters and consequently possibly to adverse environmental effects.

So far this problem has been addressed by producing formulations by mechanical compaction (e.g. pressing), coating in the fluidized bed or in coating pans with waxes, resins and polymers by microencapsulation in liquid phase or matrix encapsulation. However, these known methods exhibit numerous shortcomings.

For example mechanical compaction cannot influence substantially the solubility of the active agent, hardening of the surface just delays the water intake.

A coating in a fluidized bed or coating pan by spraying on molten or dissolved resins, waxes or polymers normally leads to a relatively inhomogeneous distribution of the coating mass on the active agents presented in form of a powder. Due to the contact of the particles in the layer with each other, moved by air agitation or mechanically, subsequently an equilibrium state between abrasion and application occurs, so that the thickness of the coating that can be applied on the active agents is limited in total.

A microencapsulation in an aqueous environment fails when using water-soluble active agents, because if the inner most of the time hydrophobic phase gets into contact with the outer aqueous phase, the active agents are at least partially dissolved and thus evade the encapsulation.

During reverse phase encapsulation, where the inner phase represents the aqueous phase and the outer phase represents the oily phase, it is necessary either to dissolve the active agents in a solvent immiscible with water, which results in the limitation of the achievable maximum concentration, or the active agents have to be present in molten form, which is not always possible or desirable. Moreover alteration of the form of the molten active agents during recrystallization after encapsulation can lead to bursting of the capsule, in which case the protection is lost to a large extent.

In a matrix encapsulation where the particles of the active agent in solid form are enclosed by an outer continuous phase and afterwards have to be treated mechanically by crushing, grinding or milling, the previously protected particles are logically partially exposed again by this comminution process and protection is lost to a large extent as well.

DE 10 2010 028826 A1 discloses a method for preparing microcapsules containing active agents with encapsulation of the active agents by polymerization reaction, wherein the microcapsules are based on epoxy resins, and under reaction conditions the active agent may be present either as a liquid or as a solid.

From EP 0841088 A2 microcapsules are known, the walls of which consist of reaction products of amino groups containing crosslinkers with isocyanates or contain such reaction products. The microcapsules produced in this manner, which usually have a diameter in the range of 3-25 μm, are used for carbonless copy paper. As usual the method used is based on the chemical principle of interfacial polymerization or interfacial polyaddition, wherein the substances to be encapsulated are dissolved in a hydrophobic oil, mixed with a polyisocyanate capable of forming a wall and are then processed with water to form an oil-in-water emulsion. This emulsion is then mixed with the crosslinking agents, whereby a polymer film is formed at the interface between oil and water. The possible uses of di- or polyamines, diols, polyols and amino alcohols with functional policy as crosslinkers are mentioned. A similar prior art is also known from DE 10 2004 059977 A1, wherein the prepared microcapsules are usable in electrophoretic image display devices. Again, the principle of interfacial polymerization or interfacial polyaddition is employed, wherein an oil-in-water emulsion is processed just as in the method according to DE 10 2010 028826 A1.

WO 2012/069805 A1 discloses a method for preparing a dispersion from encapsulated solid particles in a carrier which is mainly prepared from organic liquid, which method comprises the steps of providing a dispersion comprising a particulate solid, a liquid medium and a polymer dispersant with at least 3.0 mmol reactive groups per gram of dispersant, the cross-linking of the polymer dispersant via at least some of these reactive groups, whereby the particulate solid is encapsulated by the cross-linked polymer dispersant, and covalently binding of an agent providing end groups to the polymer dispersant via the (remaining) reactive groups, such that the remaining organic liquid carrier comprises one or more organic liquids and optionally water, provided that the dispersion does not contain more than 30 weight percent of water.

It is understood that these known techniques for water-soluble active agents are not usable or only in a very limited way.

The closest prior art for the subject matter of the present invention is U.S. Pat. No. 5,911,923 B1 (Work et al.), which discloses the possible encapsulation of a solid active agent. The document concerns a method for microencapsulating an active agent, wherein the active agent is dispersed in an organic continuous phase and a polyfunctional isocyanate and a diol or polyol is added in the presence of an optional polymerization catalyst. Suitable isocyanates are described, among those also phenylene diisocyanate, suitable diols are mentioned as well.

Object of the present invention is now to provide concentrates of water-soluble active agents, which active agents are coated in solid, crystalline or microcrystalline form or in a form bound to amorphous, microporous particles, such that each individual particle is coated with a defined protective layer of uniform thickness, whereby a defined, reproducible permanent hydrophobization is achieved. When in the following the term "active agent" is used, it also means a mixture of different active agents. Similarly, the term "crystals of an active agent" means an active agent or mixture of active agents in solid, crystalline or microcrystalline form or in a form bound to amorphous, microporous particles.

The solution of the invention consists of evenly distributing the crystals of an active agents in an anhydrous method using solid active agents as starting material in a first organic solvent with addition of a dispersant, optionally adjusting the viscosity of the resulting solution with a suitable additive, adding of a polymer forming agent optionally in a second organic solvent to the obtained solution, whereby the viscosity of either the solution to be added or the resulting solution is optionally adjusted by adding a suitable auxiliary, and adding a crosslinking agent having at least two functional groups in a third organic solvent to the obtained solution, where again the viscosity of either the solution to be added or the resulting solution is optionally adjusted by adding a suitable auxiliary. The polymer forming agents are polymethylene polyphenyl isocyanates of the type "polymeric MDI" with low viscosity with a medium NCO content (25-35, particularly preferred 30-32%), like for example the products Voranate M220 of Dow Chemical, as well as Suprasec 5025 of Huntsman. Toluene diisocyanate (TDI) has also been identified as suitable polymer forming agent, and here again the types with low viscosity and low acidity like for example the product Voranate T-80 of Dow Chemical is preferred. Products with higher viscosity have to be diluted first with said organic solvents, however this leads to an unfavorable mixing ratio between the concentration of the active agent and the concentration of the polymer forming agent.

The suspension obtained by the addition of a dispersant is preferably kept homogeneous by suitable stirring and/or dispersing tools, while the polymer forming agent is added so slowly that no local reaction in the form of aggregations (clumping) occurs. If necessary, the polymer forming agent can also be diluted with suitable solvents and/or are emulsified with the help of dispersing agents suitable for this purpose. The suspension with the crosslinking agent is kept at reaction temperature and vigorous stirring is continued until the polycondensation process is largely completed. This is the case when the coated crystals formed have lost their surface stickiness and therefore no longer agglomerate together after switching off the stirrer and a free-flowing, lump-free suspension is maintained. This suspension containing the now finished coated, discrete crystals of the active agent is cooled to room temperature and can be converted into a saleable product by the addition of suitable dispersing and stabilizing agents, or optionally subjected to further process steps for obtaining a dry powder or granulate. For the direct use of the suspension fumed silica of the type Aerosil® 200 of the company Evonik and precipitated silicas of the type Sipemat® 22 from Evonik have proven to be particularly suitable stabilizing agents. If a subsequent spontaneous emulsification is to take place in water, the addition of suitable emulsifiers is required. For this purpose, ethoxylated $C_{11}$-$C_{15}$ technical alcohols, for example of the type Tergitol® 15 S 7 of the company Dow, polyoxyethylene oeyl ether of the types Brij® 05 and O10 of the company Croda, as well as polyethylene glycol esters of fatty acids of the type Geronol® VO 2003 of the company Rhodia have proven to be particularly suitable. For the transformation of the suspension into a dry formulation absorption and drying processes known in the state of the art can principally be used, in particular vacuum drying, spray drying as well as fluidized bed drying and fluidized bed granulation, if necessary with the addition of suitable protective colloids, binders, wetting agents and fillers, each optionally with partial evaporation upstream and at least partial or even better complete solvent recovery. The entire process of the invention can take place atmospherically open, but depending on the vapor pressure and flash point of the selected solvent partially or completely under an inert gas or under positive pressure or negative pressure, wherein the preferred embodiment according to the invention is in-situ coating under atmospheric pressure while avoiding a potentially explosive atmosphere by selecting a suitable solvent. A possible, but not urgently necessary additional acceleration of the polycondensation by using physical methods such as continuous mixing processes, thin-film reactors, UV irradiation or sonication is also explicitly part of the invention.

Suitable substrates for coating are in principle such active agents, which are not present in molten form at the reaction temperature and have a surface compatible with the polymer forming agent, which means that they are not chemically attacked by it. Also multilayered particles and microporous particles with agents optionally absorbed therein can be considered as substrates. Here active agents are understood as generally biologically active, in particular insecticidal, herbicidal, fungicidal, acaricidal, algaecidal, microbicidal, microbistatic, rodenticidal, antibiotically active agents, and repellents, attractants, pheromones and generally attracting or repelling fragrances or flavors as well as mixtures of such agents. It is preferred that prior to coating the active agent is sized to a particle size of 1-500 μm, preferably 3-50 μm, which is suitable for the in situ polycondensation. This can vary depending on the physico-chemical properties, such as melting point, boiling point, hardness, minimum ignition power, flammability, specific conductivity, etc., and can be achieved by dry or preferably by wet milling, for example in a pin mill, jet mill or ball mill.

The dispersant serves to keep the spacing of the crystals of the used active agents in the first organic solvent from one another to enable the subsequent encapsulation of the crystals of the active agent or to emulsify the polymer-forming agent in the optionally used second organic solvent. Particularly suitable dispersant are polyvinyl pyrrolidone derivatives, in particular of the company ISP, especially in the form of Agrimer® AL 22 and Surfadone® LP 100 or 300. Of course the dispersant has to be compatible with the used solvents.

The used solvents must have a specific low viscosity, the active agent or, as the case may be the mixture of active agents has to be insoluble in the solvents, the solvents must be free from hydroxyl and/or amino groups and the polymer forming agent or the crosslinking agent must be soluble in their respective solvents. The requirements can also be met by a single solvent, i.e. the first, second and third organic solvent may be identical. Among substances worth considering for this purpose are specifically esters of vegetable oils, particularly methyl esters and ethylhexyl esters of saturated, possibly mono- or polyunsaturated medium-chain fatty acids having 8 to 16 carbon atoms, but without any reactive hydroxyl groups. Such suitable solvents are marketed for example under the trade name Radia® 7118 of the company Oleon. In those cases where these preferred solvents are not suitable for the active agent to be coated due to their dissolving properties, other solvents, such as terpene hydrocarbons, in particular orange terpene, but also aliphatic and aromatic hydrocarbons, as well as ethers and esters of natural and industrial aliphatic and aromatic alcohols in branched or unbranched form as well as mixtures of such solvents can be used. In contrast, mono- and polyhydric alcohols, polyols, amines, quats and generally highly polar or ionic solvents have been proven to be unsuitable with the polymer forming agent due to their reactivity. Preferably the organic solvent is Surfadone® LP 300, orange terpene and/or tributyl citrate.

Preferably, the polymer forming agent is added in the amount required for the desired coating thickness. This amount depends on the concentration of the suspension of the active agent, the particle size as well as layer thickness which is necessary for the hydrophobization. The quantity ratio between active agent and polymer forming agent can be from 0.1% to 500%, but preferably 15% to 100%, respectively, expressed as percent by mass with regard to the active substance.

Preferably, the reaction according to the invention takes place at a temperature between 10 and 80, preferably between 40 and 60° C., or at a temperature of at least 1° C., more preferably at least 5° C., particularly preferably more than 10° C. below the flash point of the respectively used organic solvent and/or at a temperature at which the used solvent or solvents have such a low vapor pressure that under reaction conditions no potentially explosive atmosphere arises.

According to a preferred embodiment of the present invention, the crosslinking agent is at least a bifunctional cross-linker for NCO groups and is added in at least a stoichiometric amount, so that all of the NCO groups of the polymer forming agent are crosslinked, thereby forming in situ a polyurethane layer on the surface of the particles of the active agent. According to literature, suitable reaction partners for NCO groups would be polyhydric alcohols, polyols, di-, tri-, and polyamines, and mixtures thereof, which are soluble in the selected solvent and do not react chemically with it. Surprisingly ethanolamines, particularly triethanolamine (TEA) have proven to be especially suitable reactants. In principle reactants known from literature, such as DETA (diethylenetriamine), EDA (ethylenediamine), TEDA (triethylenediamine), HMD (hexamethylenediamine), can also be used, but lead to less favorable characteristics of the polyurethane layers, especially to a lower mechanical strength.

The present invention will now be further illustrated by the following examples to which, however it is not limited.

EXAMPLE 1

Basics

In the following steps a coating of Acetamiprid-crystals with a hydrophobic layer of polyurethane is described:
I. 50 g of dry-milled Acetamiprid with an average particle size d50 of 5-6 µm is dispersed into a solution of 142 g Radia® 7118 (methyl laurate) of Oleon NV (NL) and 2.9 g Agrimer® AL 22 (an alkylated polyvinylpyrrolidone) of ISP International Specialty Products (US) at room temperature with a high shear mixer and then heated to 50° C.
II. A mixture consisting of 9.4 g Voranate® M 220 (polymethylene polyphenyl isocyanate) of The Dow Chemical Company (US) and 3.5 g Surfadonee® LP 300 (linear N-alkyl-2-pyrrolidone) of ISP International Specialty Products (US) is then slowly added dropwise to the dispersion and then the mixture is stirred for 10 minutes.
III. A solution is prepares from 3.7 g of triethanolamine (TEA) and 9.4 g Surfadonee® LP 300 and this is very slowly added dropwise over a period of about 60 minutes.
IV. For a sufficient reaction rate, the temperature is kept between 50 and 60° C. After about 10 minutes, the reaction begins to start and the solution begins to thicken. In order to avoid an excessive thickening of the suspension during the coating reaction, the solution isd stirred vigorously with an Ultra Turrax® homogenizer of IKA Werke GmbH & Co. KG (DE). Inadequate stirring during the reaction leads to the formation of polymer lumps, which may result in a non-homogeneous coating.
V. Then the dispersion is stirred for 2 further hours at 50° C. and then cooled again to room temperature.

In order to determine the level or the quality of the coating, the prepared dispersion is dispersed into a liquid water-based building protection film in such an amount that the content of Acetamiprid in the finished film is 2 g/kg.

4 g of this liquid film, corresponding to 8 mg coated Acetamiprid are then extracted in 100 ml of water and the content of acetamiprid is determined with HPLC-UV.

The following results were determined.

| Extraction time | Acetamiprid in solution mg/100 mol | Acetamiprid dissolved |
| --- | --- | --- |
| 30 minutes | 1.04 | 13% |
| 24 hours | 2.40 | 30% |
| 48 hours | 2.64 | 33% |
| 7 days | 2.96 | 37% |

According to literature Acetamiprid has normally a solubility of 400 mg/100 ml at 20° C. From the results listed in the table above it becomes clear that the solubility was reduced significantly by the coating of the crystals.

EXAMPLE 2

Regulation of the Hydrophobization by the Amount of Polymer Forming Agent

In this example, the amount of polymer forming agent is doubled compared with Example 1, furthermore the coating was carried out in orange terpene as solvent.
I. 50 g of ground Acetamiprid with an average particle size of 5-6 µm is dispersed into a solution consisting of 135 g of orange terpene and 2.5 Agrimer® AL 22 at room temperature using a high shear mixer and then the solution is heated up to 45° C.
II. 25.2 g Voranate® M 220 are mixed with 25.2 g Citrofol® B1 (acetyltributyl citrate) of Jungbunzlauer (AT) and slowly added dropwise to the dispersion.
III. 9.2 g of triethanolamine are slowly added dropwise under high shear mixing of the dispersion over a period of 60 minutes. The dispersion is constantly agitated.
IV. The reaction is completed when the solution does not thicken any more when the mixing is stopped. This is the case after further 30 minutes of stirring.
V. After the end of the reaction the dispersion is stirred for 2 hours at 40° C.

The quality of the coating was examined using the same method as described in Example 1.

| Extraction time | Acetramiprid in solution mg/100 ml | Acetamiprid dissolved |
|---|---|---|
| 30 Minutes | 0.40 | 5% |
| 24 Hours | 0.72 | 9% |
| 48 Hours | 0.80 | 10% |
| 7 Days | 1.20 | 15% |

In this case, the doubling of the polymer also results in a doubling of the hydrophobization of the crystals of the active agent. It can also be demonstrated by this example that the coating works in another solvent medium.

EXAMPLE 3

Definition of the Quantity Range

Here, the amount of polymer forming agent is reduced by 50% compared to Example 1.

This experiment is carried out corresponding to example 1. However, the amount of Voranate M 220® is reduced from 9.2 g to 4.6 g and the amount of triethanolamine is reduced from 3.7 g to 1.85 g.

Quality tests as described in example 1 and 2 revealed that after 30 minutes already 100% of the Acetamiprid is dissolved. Therefore the coating is insufficient.

EXAMPLE 4

Definition of the Temperature Range

Amounts and reagents correspond to those of example 1, but here the entire batch is cooled to keep the temperature during the coating process constantly under 15° C. The result of this is that the reaction starts only after 2 hours and proceeds very slowly. Besides the solution thickens very much in spite of intensive stirring, so that a compact paste is produced.

The reason for this behavior is the increasing viscosity of the dispersion at low temperatures, causing the particles to clump together. Therefore, dispersion media with low viscosity are preferred for carrying out the coating at low temperatures.

The quality of the obtained capsule is very similar to that of Example 1.

EXAMPLE 5

Effect of Changing the Cross-Linking Agent

The same production method as in example 1 was chosen but using diethanolamine instead of triethanolamine as a crosslinking agent. The resulting high increase in viscosity of the solution during the coating process leads to a rather doughy mass. Crystals are not sufficiently coated with the polymer.

Quality tests as described for example 1 and 2 revealed that already after 30 minutes 80% of the Acetamiprid is dissolved.

EXAMPLE 6

Effect of Changing the Solvent

In this experiment an attempt was made to coat the Acetamiprid crystals using a different vegetable oil ester, ethylhexyl oleate (Radia® 7331 of the company Oleon) as solvent. Due to insufficient miscibility and likely reaction of the polymer forming agent with this solvent there was no sufficient coating of the crystals and the attempt had to be stopped.

EXAMPLE 7

Coating of Acetamiprid With 18.89 G of Polymer/100 G Acetamiprid

This test is based on the basics of Example 1, wherein the steps are as set forth therein. The slightly higher temperature of 60° C. is chosen.

| Component | Quantity |
|---|---|
| Radia ® 7118 | 509.0 g |
| Agrimer ® AL 22 | 10.3 g |
| Heat up to 60° C. - | |
| Ground Acetamiprid @ 98.0% | 180.0 g |
| Disperse with Ultra Turrax ® - | |
| Premix of polymer forming agents (see below) | 47.5 g |
| Add slowly, stir for 10 min - | |
| Premix crosslinker (see below) | 44.3 g |
| Add slowly over 30 min, stir vigorously - | |
| Hold temperature for 1 h at 60° C. - | |
| Radia ® 7118 | 80.0 g |
| Allow to cool to room temperature and stir overnight - | |
| Total | 871.0 g |

| | Quantity |
|---|---|
| Polymer forming agent Premix | |
| Surfadonee ® LP 300 | 10.3 g |
| Voranate ® M220 | 34.0 g |
| Total | 44.3 g |
| Crosslinker Premix | |
| Surfadone ® LP 300 | 34.0 g |
| Triethanolamine (TEA) @ 100.0% | 13.4 g |
| Total | 47.5 g |

EXAMPLE 8

Coating of Acetamiprid With 9.44 G Polymer/100 G Acetamiprid

The amounts of polymer forming agent premix and crosslinker premix were cut in half compared with example 7, therefore the calculated amount of coating was cut in half as well.

| Component | Quantity |
|---|---|
| Radia ® 7118 | 554.9 g |
| Agrimer ® AL 22 | 10.3 g |
| Heat up to 60° C. - | |
| Ground Acetamiprid 98.0% | 180.0 g |
| Disperse at Turrax ® - | |
| Premix polymer forming agent (see below) | 23.73 g |
| Add slowly, stir for about 10 minutes | |

| Component | Quantity |
|---|---|
| Premix crosslinker (see below) | 22.1 g |
| Add slowly within 15 min - | |
| Keep temperature for 1 h at 60-65° C. - | |
| Radia ® 7118 | 80.0 g |
| Allow to cool to room temperature and stir overnight - | |
| Total | 871.0 g |

| | Quantity |
|---|---|
| Polymer forming agent Premix | |
| Surfadonee ® LP 300 | 5.1 g |
| Voranate ® M220 | 17.0 g |
| Total | 22.1 g |
| Crosslinkers Premix | |
| Surfadonee ® LP 300 | 17.0 g |
| Triethanolamine (TEA) @ 100.0% | 6.7 g |
| Total | 23.7 g |

The example of U.S. Pat. No. 5,911,923 B1 was carried out for comparative purposes, however the obtained dispersion of microcapsules in the solvent used according to U.S. Pat. No. 5,911,923 B1 (a mixture of toluene, ethyl acetate and soybean oil), proved not to be stable, furthermore the obtained microcapsules exhibited only a low wall thickness, therefore the active agent could diffuse quickly through it. When using the solvent preferably used according to the invention a significant improvement was obtained already. Example 9 shows the method according to U.S. Pat. No. 5,911,923 B1 using the preferred solvent according to the invention (but without the use of diamines as a cross-linking agent) with an already substantially improved encapsulation of the active agent used.

EXAMPLE 9

Coating of Acetamiprid With 18.89 g of Polymer/100 g of Acetamiprid)

In this experiment a diol was used (in this case propylene glycol) instead of the amino alcohol preferred according to the invention, wherein the polymerization reaction is conducted in the presence of a polymerization catalyst. Here 1,4-diazabicyclo[2.2.2]octane serves as catalyst, which is commonly used in the preparation of polyurethanes. The calculated coating thickness is the same as in example 7.

| Component | Quantity |
|---|---|
| Radia ® 7118 | 512.2 g |
| Agrimer ® AL 22 | 10.3 g |
| Heat to 60-65° C. - | |
| Ground Acetamiprid @ 98.0% | 180.0 g |
| Disperse well at Turrax ® - | |

| Component | Quantity |
|---|---|
| Premix polymer forming agent (see below) | 44.30 g |
| Add slowly and stir for about 10 minutes - | |
| Crosslinker catalyst premix (see below) | 44.3 g |
| Add slowly dropwise at 60-65° C. - | |
| Total | 791.0 g |
| Yield | 791.0 ml |

| | Quantity |
|---|---|
| Polymer forming agent Premix | |
| Surfadone ® LP 300 | 10.3 g |
| Voranate ® M220 | 34.0 g |
| Total | 44.3 g |
| Yield | 44.3 ml |
| Crosslinker Catalyst Premix | |
| Surfadone ® LP 300 | 34.0 g |
| Propylene glycol | 9.5 g |
| DABCO | 0.8 g |
| Total | 44.3 g |
| Yield | 44.3 ml |

EXAMPLE 10

Comparative Example, Not According to the Invention, Typical Micro-Encapsulation According to the O/W Emulsion Process For Obtaining 16.00 G Of Polymer/100 G of Acetamiprid This is a typical way of drug encapsulation not according to the invention, as it would be carried out by someone skilled in the art on the basis of published literature. In the process the active substance Acetamiprid is dissolved in a water-immiscible solvent (organic phase) and emulsified in an aqueous medium (water phase), wherein the disadvantage is that the water already solves part of the Acetamiprid during emulsification. Polyisocyanate was used as encapsulating polymer, which engages with a diamine as cross-linking agent in surface polymerization and thus forms a shell of polyurea.

| Component | Quantity |
|---|---|
| Water phase @ 50° C. | 939 g |
| Oil phase @ 60° C. | 610 g |
| Ethylenediamine solution 20% strength | 17 g |
| Encapsulate with Turrax ® - | |
| Stir for 2 h at 50° C. - | |
| Silfoam ®SRE, antifoam of Wacker Chemie AG, DE | |
| An antifoaming agent | 15.1 g |
| Glucopon ®215 UP BASF (DE) | |
| a non-ionic surfactant | 56 g |
| the rest was left out | |

-continued

| Component | Quantity |
|---|---|
| Proxel ® GXL from Lonza (IT), a biocide | 4.0 g |
| Citric acid | 7.9 g |
| Demineralized water | 126.6 g |
| Rhodopol ® of Brenntag (AT), Xanthan gum 23 at 2% | 183 g |
| Total | 1958 g |
| Yield | 1958 ml |

| Oil phase | Quantity |
|---|---|
| Purasolv ® EHL, 2-ethylhexyl-L-lactate | 395 g |
| Voranate ® M 220 | 16 g |
| Acetamiprid | 100 g |
| Purasolv ® EHL | 99 g |
| Total | 610 g |
| Yield | 610 ml |

| Water phase | Quantity |
|---|---|
| Demineralized water | 713 g |
| Silfoam (TM) SRE | 0.5 g |
| Agrimer ® AL-10 LC | 11.9 g |
| Glucopon ® 215 UP | 3.7 g |
| PVP K-30 ®' water-soluble polyvinylpyrrolidone | 32 g |
| Silfoam ® SRE, antifoam | 0.3 g |
| Demineralized water | 178 g |
| Total | 939 g |
| Yield | 939 ml |

The last 4 examples 7 to 10 will now be compared for their encapsulating quality. For this purpose the liquid building protection film which was already mentioned in the quality control of example 1 and 2 with a content of 2 g/kg Acetamiprid is prepared and dried. The dried film is then extracted with 100 ml of water and the amount of Acetamiprid dissolved in the water is analytically determined over time.

QUALITY CONTROL OF EXAMPLE 7

Embodiment of the Invention With Tea and 18.89 G of Polymer/100 G Acetamiprid

| Extraction time | Weighed sample [g] | Content in the film [g/kg] | Acetamiprid in solution [mg/100 ml] | Dissolved Acetamiprid |
|---|---|---|---|---|
| 30 Minutes | 6.4 | 2.2 | 1.085 | 8% |
| 24 Hours | 6.4 | 2.2 | 1.8 | 13% |
| 48 Hours | 6.4 | 2.2 | 2.2 | 16% |

QUALITY CONTROL OF EXAMPLE 8

Embodiment of the Invention With Tea; 9.44 G of Polymer/100 G Acetamiprid

| Extraction time | Weighed sample [g] | Content in the film [g/kg] | Acetamiprid in solution [mg/100 ml] | Dissolved Acetamiprid |
|---|---|---|---|---|
| 30 Minutes | 5.7 | 2 | 10.5 | 92% |
| 24 Hours | 5.7 | 2 | 10.5 | 92% |
| 48 Hours | 5.7 | 2 | — | — |

QUALITY CONTROL OF EXAMPLE 9

Embodiment With Diol and Dabco; 18.89 G of Polymer/100 G Acetamiprid

| Extraction time | Weighed sample [g] | Content in the film [g/kg] | Acetamiprid in solution [mg/100 ml] | Dissolved Acetamiprid |
|---|---|---|---|---|
| 30 Minutes | 5.4 | 2.1 | 5.3 | 47% |
| 24 Hours | 5.4 | 2.1 | 5.7 | 50% |
| 48 Hours | 5.4 | 2.1 | 6.2 | 55% |

QUALITY CONTROL OF EXAMPLE 10

Comparative Example (Embodiment Not According to the Invention With Emulsifying Process, 16.00 G of Polymer/100 G Acetamiprid)

| Extraction time | Weighed sample [g] | Content in the film [g/kg] | Acetamiprid in solution [mg/100 ml] | Dissolved Acetamiprid |
|---|---|---|---|---|
| 30 Minutes | 5.3 | 2.1 | 10 | 90% |
| 24 Hours | 5.4 | 2.1 | — | — |
| 48 Hours | 5.4 | 2.1 | — | — |

It can be seen clearly here that in the embodiment of the coating according to the invention the active ingredient is released much more slowly than in a traditional, non-inventive embodiment. If Acetamiprid is used as an active agent a solution delay which is suitable for the purpose of the building protection film occurs, starting with an amount of about 19 g polymer forming agent per 100 g Acetamiprid. Cutting the amount of polymer forming agent in half does not lead to a suitable solution delay any more as shown in Example 3 and 8.

The optimum quantity of polymer forming agent for specific application depends inter alia on the shape and average particle size of the coating substrate and it is up to the expert to determine it by means of calculations and experiments for the individual purpose.

The invention claimed is:

1. A method for the preparation of concentrates of a water-soluble active agent comprising:
   distributing crystals of an active agent in a first organic solvent or solvents in a water-free process using solid active agents as a starting material with addition of a dispersant to obtain a solution;

adding a polymer forming agent to the solution in a water-free process, wherein the polymer forming agent is a polymethylene polyphenyl isocyanate; and adding a crosslinking agent having at least two functional groups to the solution in a water-free process, either before or after the addition of the polymer forming agent, wherein the crosslinking agent is an at least bifunctional crosslinking agent for an isocyanate (NCO) group that is or comprises triethanolamine (TEA) and is added in an at least a stoichiometric amount;

wherein concentrates of a water-soluble active agent are prepared.

2. The method of claim 1, wherein the polymer forming agent is comprised in an organic solvent that is different from the first organic solvent or solvents.

3. The method of claim 1, wherein the polymethylene polyphenyl isocyanate with low viscosity has a medium NCO content of 25-35%.

4. The method of claim 3, wherein the polymethylene polyphenyl isocyanate with low viscosity has a medium NCO content of 30-32%.

5. The method of claim 1, wherein the crosslinking agent is comprised in an organic solvent that is different from the first organic solvent or solvents.

6. The method of claim 1, wherein the viscosity of the solution is adjusted by adding a suitable auxiliary at any point in the method.

7. The method of claim 1, wherein the active agent is selected from the group consisting of a biologically active agent, insecticidal agent, herbicidal agent, fungicidal agent, acaricidal agent, algaecidal agent, microbicidal agent, microbistatic agent, rodenticidal agent, antibiotic agent, repellent, attractant, pheromone, fragrance and flavor.

8. The method of claim 1, wherein the dispersant is a graft polymer of polyvinyl pyrrolidone and an alkylation group of 4 to 30 carbon atoms.

9. The method of claim 1, wherein the first organic solvent or solvents is selected from the group consisting of an ester of plant oil, terpene hydrocarbon, aliphatic or aromatic hydrocarbon, and ether or ester of a natural or technical aliphatic or aromatic alcohol in branched or unbranched form.

10. The method of claim 9, wherein at least one solvent used is selected from the group consisting of a methyl ester or ethylhexyl ester of a medium chain saturated or mono- or polyunsaturated fatty acid having 8 to 16 carbon atoms without any reactive hydroxyl group or orange terpene.

11. The method of claim 1, wherein the preparation further comprises that it takes place at a temperature between 10 and 80° C.

12. The method of claim 11, wherein the preparation further comprises that it takes place at a temperature between 40 and 60° C.

13. The method of claim 1, further defined as occurring at a temperature at which the organic solvent or solvents have such a low vapor pressure that under reaction conditions no potentially explosive atmosphere is formed.

14. A powder or granule, comprising concentrates of a water-soluble active agent obtainable by the method of claim 1.

15. The method of claim 1, wherein the dispersant is a graft polymer of polyvinyl pyrrolidone and an alkylation group of 16 carbon atoms.

\* \* \* \* \*